US00PP35312P2

(12) United States Plant Patent
Baugher

(10) Patent No.: US PP35,312 P2
(45) Date of Patent: Aug. 15, 2023

(54) APPLE TREE NAMED 'DRF 28 CLTV.'

(50) Latin Name: ***Malus* x *domestica***
Varietal Denomination: DRF 28 Cltv.

(71) Applicant: Adams County Nursery, Inc., Aspers, PA (US)

(72) Inventor: John H. Baugher, Aspers, PA (US)

(73) Assignee: ADAMS COUNTY NURSERY, INC., Aspers, PA (US)

( * ) Notice: Subject to any disclaimer, the term of this patent is extended or adjusted under 35 U.S.C. 154(b) by 0 days.

(21) Appl. No.: 17/979,073

(22) Filed: Nov. 2, 2022

(51) Int. Cl.
*A01H 5/08* (2018.01)
*A01H 6/74* (2018.01)

(52) U.S. Cl.
USPC ..... Plt./162
CPC ..... *A01H 6/7418* (2018.05)

(58) Field of Classification Search
USPC ..... Plt./162
CPC ..... A01H 6/7418; A01H 5/08
See application file for complete search history.

*Primary Examiner* — Keith O. Robinson
(74) *Attorney, Agent, or Firm* — Daughety & Del Zoppo Co., LPA

(57) ABSTRACT

A new and distinct apple variety of gala named 'DRF 28 Cltv.' is provided. This variety is distinguished from other apple varieties by its unique combination of finish and color as compared to other Galas in its season.

6 Drawing Sheets

Latin name of genus and species: *Malus* x *domestica*.
Variety denomination: 'DRF 28 Cltv.'.

BACKGROUND OF THE INVENTION

The present invention relates to a new and distinct variety of apple tree named 'DRF 28 Cltv.' that resulted from a sport limb mutation of 'Fulford Gala' (U.S. Plant Pat. No. 7,589). The new variety has a similar finish to 'Fulford Gala' with a red striped coloration (RHS46A), while the 'Fulford Gala' fruit has a blush coloration. The resulting tree was selected when growing in a cultivated area in a commercial orchard in Aspers, Pa.

BRIEF DESCRIPTION OF THE DRAWINGS

This new variety is illustrated by the accompanying photographic drawings of the 'DRF 28 Cltv.' plant at approximately four (4) years old, depicting the apple tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
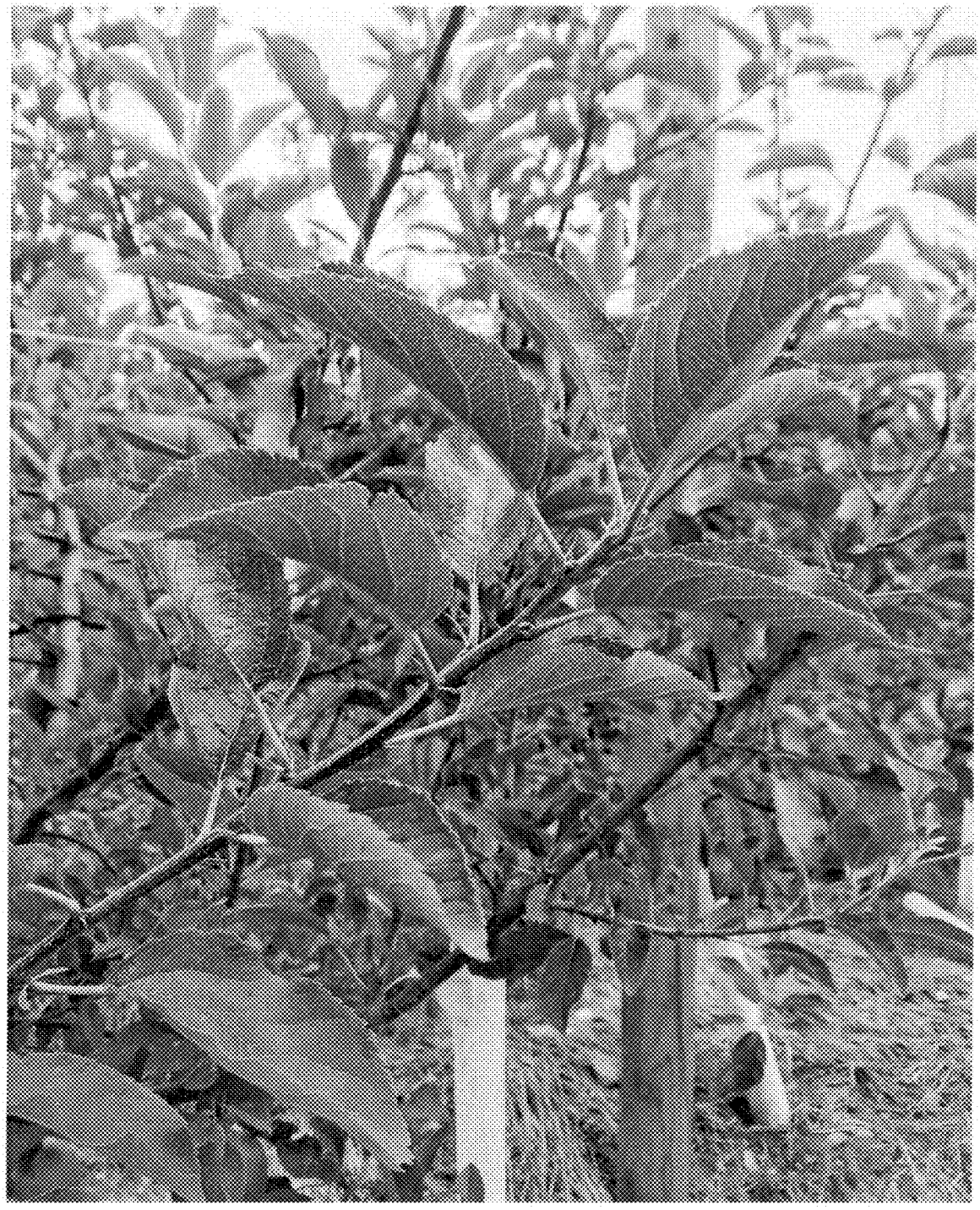
FIG. 1 is a color photograph taken on Aug. 21, 2019, of a characteristic twig of 'DRF 28 Cltv.' bearing typical leaves of the foliage.
Figure 2:
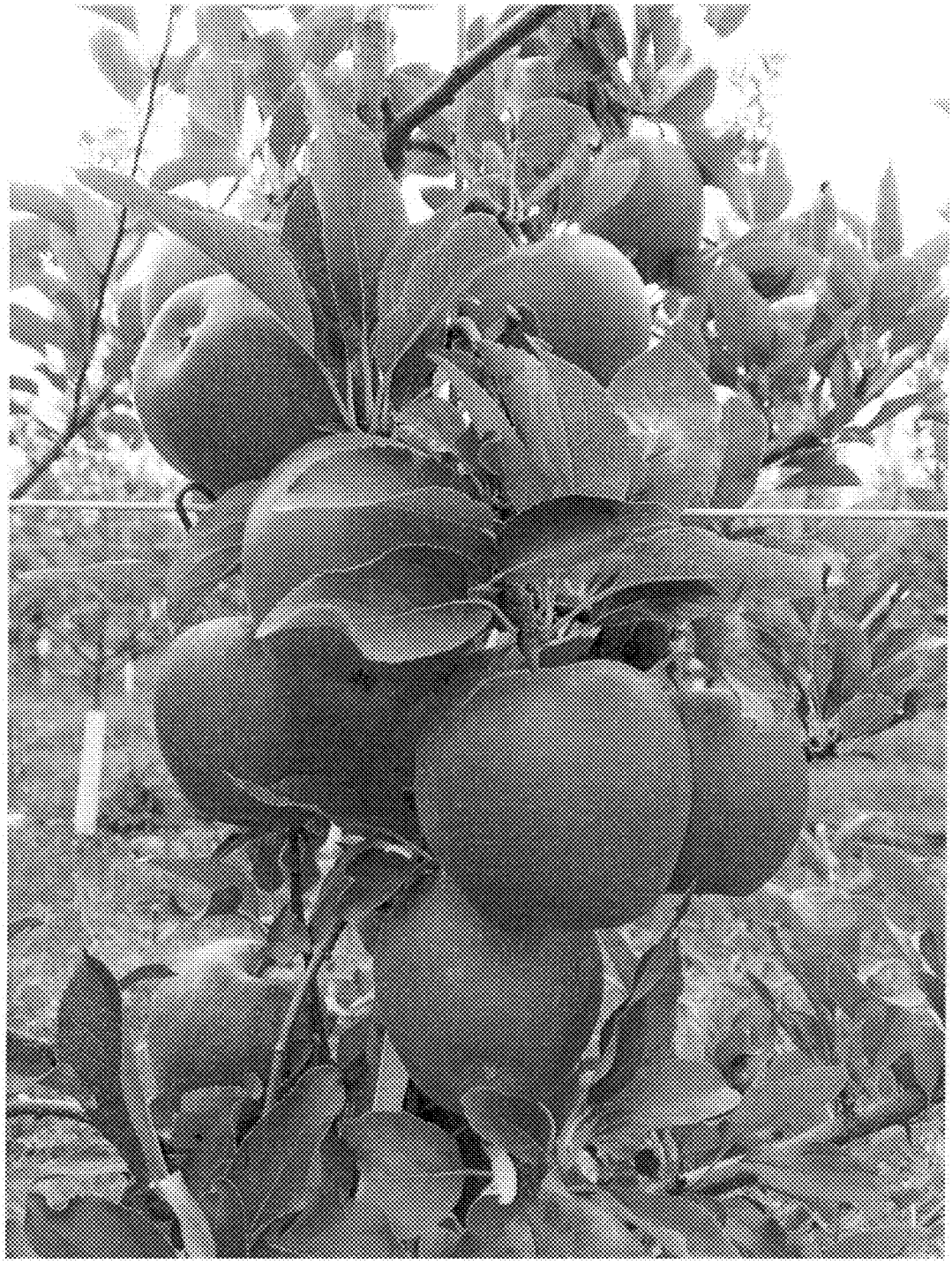
FIG. 2 is a color photograph taken on Aug. 21, 2019, of characteristic mature fruit of 'DRF 28 Cltv.' on the tree.
Figure 3:
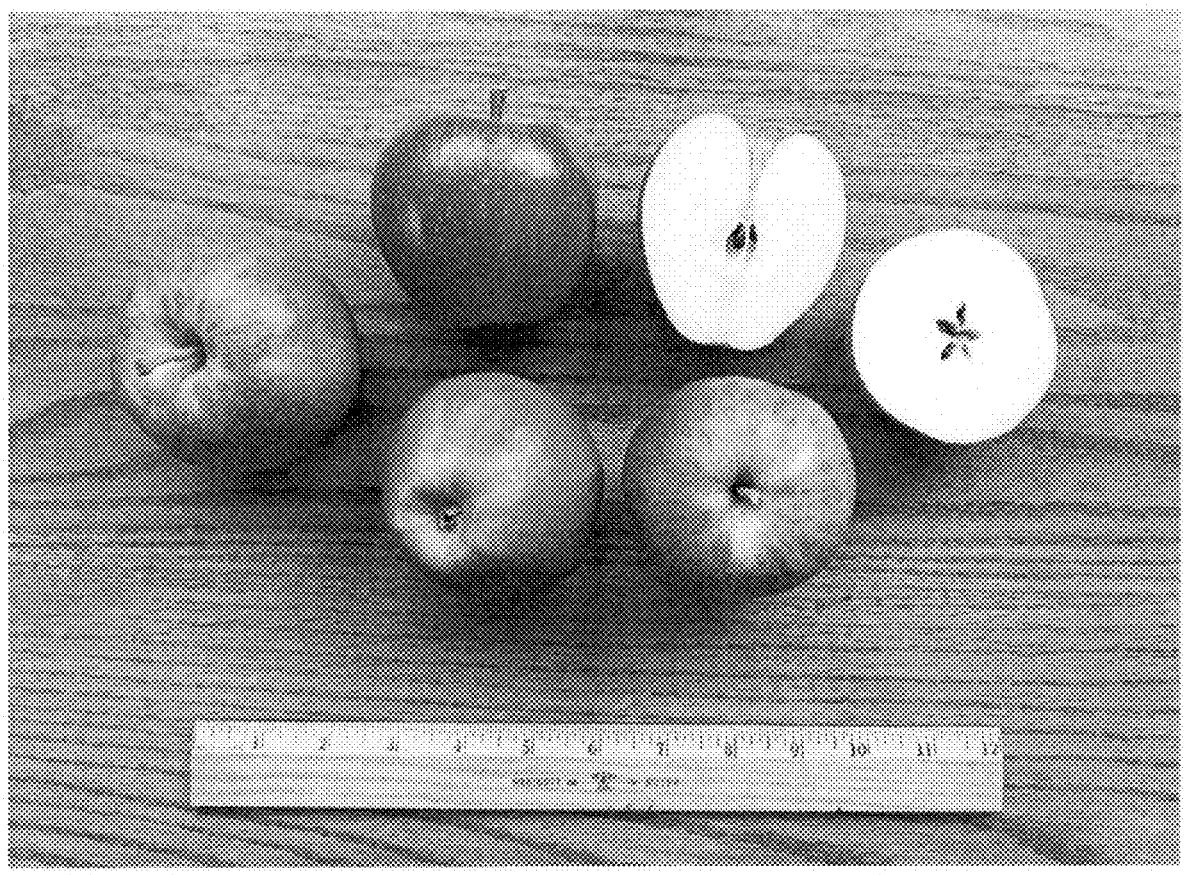
FIG. 3 is a color photograph taken on Aug. 21, 2019. Whole fruit are presented in three positions and both a transverse and longitudinal cross section.
Figure 4:
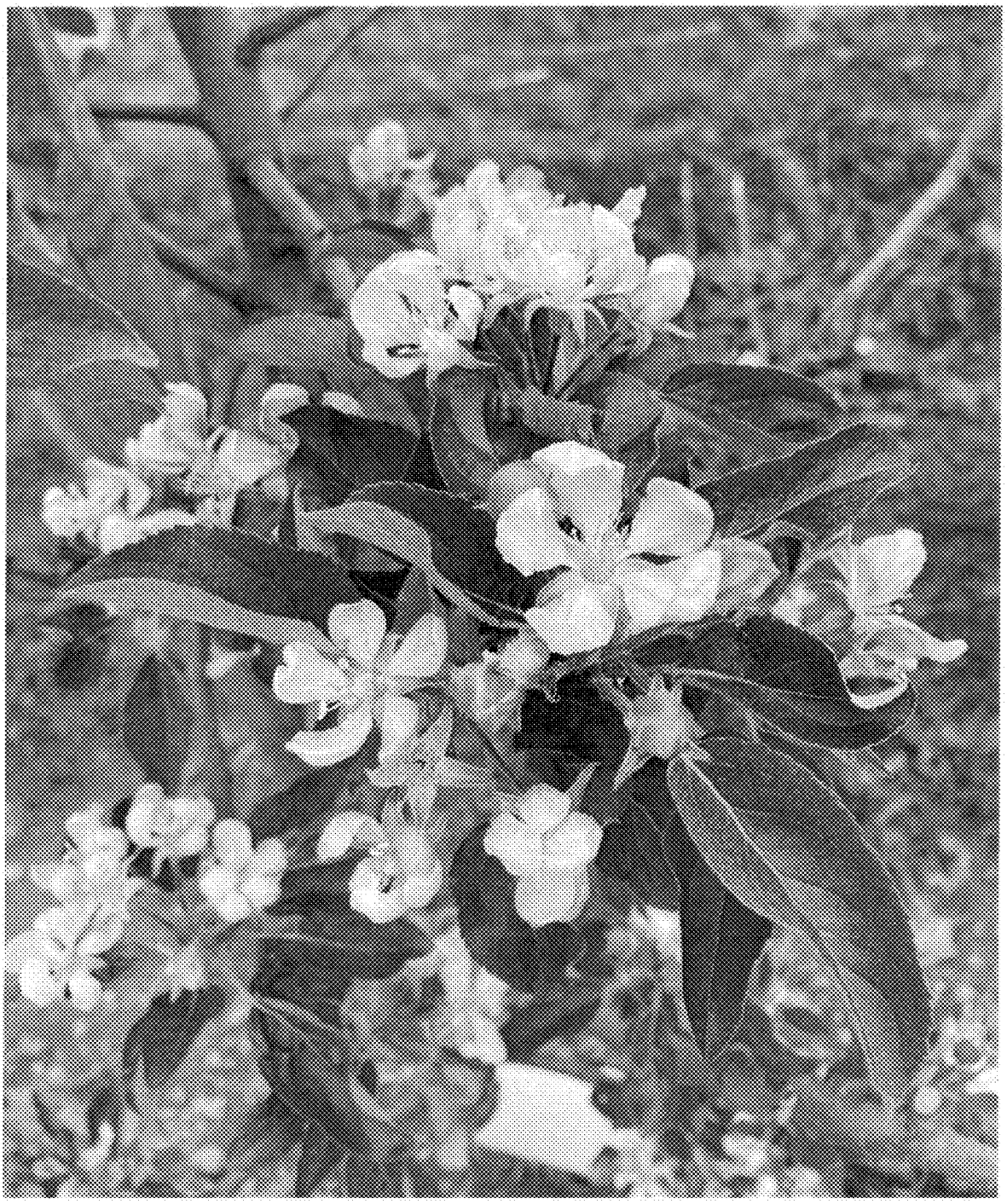
FIG. 4 is a color photograph of a characteristic twig that illustrates the typical open flowers and flower buds of 'DRF 28 Cltv.' observed on a tree in a trial block in a commercial setting in Aspers, Pa. on Apr. 29, 2020.
Figure 5:
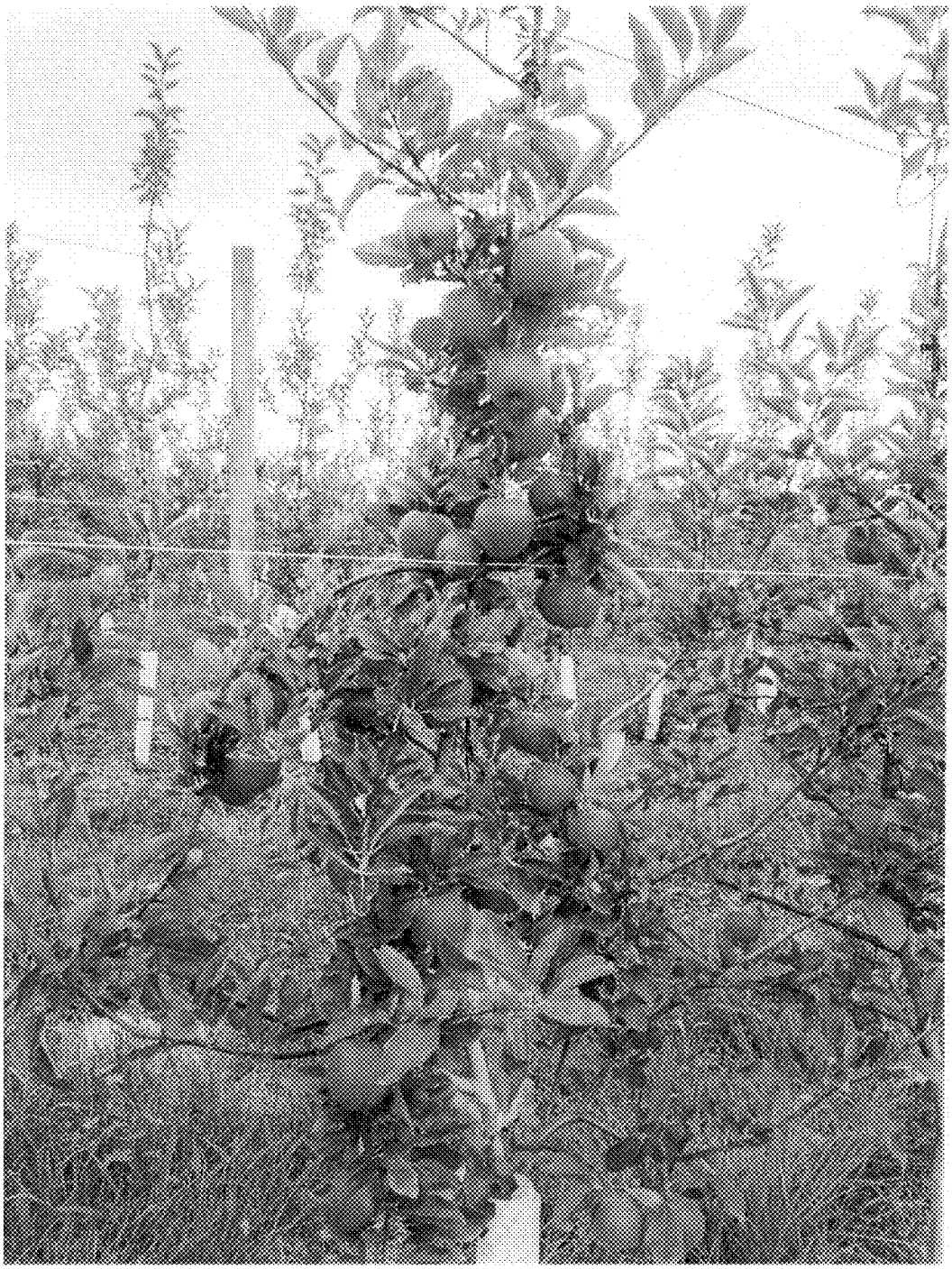
FIG. 5 is a color photograph of a tree of 'DRF 28 Cltv.', in mid-summer that illustrates the upright growth habit of a tree in a trial block in a commercial setting in Aspers, Pa. on Aug. 21, 2019.
Figure 6:
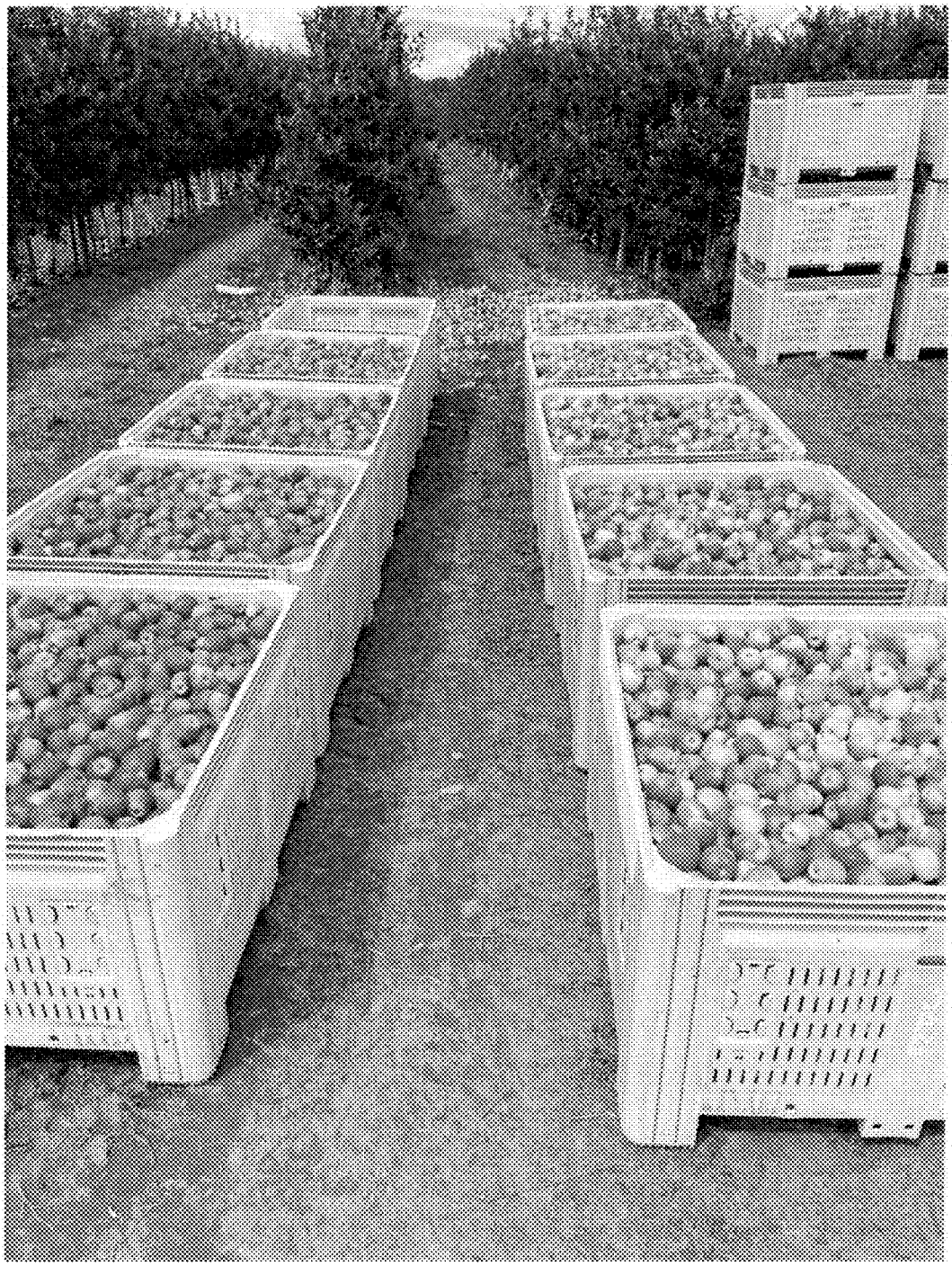
FIG. 6 is a color photograph of bins of 'DRF 28 Cltv.' on left and 'Simmons Gala' (U.S. Plant Pat. No. 10,840) on right, both picked on Sep. 23, 2021, to illustrate the color difference between the varieties.

The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

The 'DRF 28 Cltv.' variety is distinguished from other apple varieties due to the following unique combination of characteristics:

The fruit has superior coloring over other galas in its season, with an average of 10-15% more overcolor red striping (RHS 46A) than 'Simmons Gala' (U.S. Plant Pat. No. 10,840) in Adams County, Pa.

The variety was asexually reproduced in a commercial orchard in Aspers, Pa. Asexual reproduction of this new variety by grafting onto M9(Nic 29) rootstock (non-patented) shows that the foregoing characteristics are so reproduced.

The following detailed description of the 'DRF 28 Cltv.' variety is based on observations of an asexually reproduced tree. The observed tree was four (4) years of age and growing on M9/NIC 29 rootstock (non-patented) in a commercial orchard in Aspers, Pa. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to *The Royal Horticultural Society* (*R.H.S.*) *Colour Chart* (1966 Ed.)

Scientific name: *Malus* x *domestica* Borkh.

Parentage: Sport limb mutation in a planting of 'Fulford Gala' trees. Asexually reproduced by top-working and also bud grafting.

Tree:

*Vigor*.—Medium.

*Plant hardiness zone*.—Growth of plants has been observed in zone 6b.

*Dormant flower bud cold tolerance*.—At least to −17° C.

*Overall shape*.—Ramified, upright-spreading.

*Height*.—8 ft.

*Width*.—4.5 ft.

Trunk and branches:

*Trunk bark color*.—Greyed-brown (RHS 199A).

*Primary branches*.—Average 3-5 mm. in diameter and grey-orange (RS 165A) in color.

*Branch angle*.—Typically about 40 to 55 degrees.

*Lenticels*.—Approximately 10-12 per cm.$^2$, slightly raised, approximately 1 mm. long, greyed-orange (RHS 163D) in color.

*Terminal shoots*.—Average length approximately 30-35 cm.

*New growth bark*.—Grey-orange (RHS 165B) in color.

Leaves:

*Texture*.—Upper surface leathery; lower surface slightly velvety.

*Length*.—Typically between 7.6 cm. and 9.5 cm.

*Width*.—Typically between 3.8 cm. and 5 cm., folding upward.

*Apex*.—Slight cuspidate with pointed bottom, medium thick.

*Venation*.—Reticulate pattern.

*Margin*.—Fine, bi-serrate.

*Petioles*.—Generally, averaging 3 cm. long, and about 2 mm. in diameter at the mid-section. Color is red (RHS 53B).

*Stipules*.—Two, with an average length of 7 mm. Color is green (RHS 137A).

Leaf color:

*Upper leaf surface*.—Green (RHS 137A).

*Lower leaf surface*.—Yellow-green (RHS 147B).

*Vein*.—Yellow-green (RHS 145C).

Flowers:

*Size*.—Corolla diameter averaging about 4.5-5.25 cm.

*Petals*.—Typically five, free, ovate shape, soft texture.

*Color*.—Dormant bud is dark red-purple (RHS 58A), young flower buds are dark pink (RHS 67D), balloons are light pink (RHS 68C). Open flowers are white (RHS 155D).

*Pedicel length*.—Average 2 cm.

*Bloom season*.—Mid-season. Onset of first and full bloom Adams County, Pa. in 2020 was April 29; full bloom on May 4.

Fruit:

*Size*.—Large, averaging 7.6 cm. in diameter, and between 7.6 and 8.5 cm. high.

*Shape*.—Ellipsoid.

*Color*.—Overcolor is 90-95% red striping (RHS 46A) in color over a muted red ground color (RHS47B).

*General color effect*.—90-95% deep red striping over muted red background.

*Skin*.—Thin, smooth; glossy, waxed.

*Stem*.—Color is greyed-orange, (RHS 175C), lightly pubescent, length medium, between 1.5 to 2.2 cm., and 2 mm. in diameter.

*Cavity*.—Flaring, depth 1.9 cm., breadth between 1.7-2.5 cm. Color greyed-orange (RHS 163C).

*Basin*.—Depth between 0.65 and 1 cm.; breadth 1.9 cm.

*Calyx*.—Sepals persistent with erect tips, open, diameter 1 cm.

*Calyx tube*.—Cone-shaped.

*Lenticels*.—Size from 0.5 mm to 1.5 mm with 1-11 mm spacing between each lenticel, 1144 in number, greyed-orange (RHS 163D).

*Russet*.—Slight, mainly around cavity, greyed-orange, (RHS 163B).

Fruit properties:

*Flesh color*.—Cream (RHS 155D).

*Juice*.—Above average.

*Firmness*.—Firm.

*Texture*.—Crisp and breaking.

*Flavor*.—Sweet.

*Aroma*.—Moderately aromatic.

*Eating quality*.—Very good; time of eating maturity: early.

*Keeping quality*.—Best before 7 months of storage.

*Core*.—Sessile position; open, 2.5 cm. in diameter.

*Core lines*.—Basil, clasping.

*Carpellary area*.—Visible.

*Depth of calyx tube*.—5-7 mm.

*Seed cells*.—Generally 2 seeds per cell, closed, 5 in number.

*Cell walls*.—Thick, obovate in cross-section; length 0.95 cm., breadth 0.5 cm.

Seeds:

*Number*.—Usually 10.

*Length*.—0.9 cm.

*Breadth*.—0.3 cm.

*Form*.—Acute.

*Color*.—Greyed-orange (RHS 166A).

*Plant/fruit disease and pest resistance/susceptibility*.—Good, susceptible to mildew (*Podosphaera leucotricha*), scab (*Venturia inaequalis*) and fire-blight (*Erwinia amylovora*).

I claim:

1. A new and distinct variety of apple tree named 'DRF 28 Cltv.', substantially as herein shown and described.

* * * * *